(12) United States Patent
Sadowsky et al.

(10) Patent No.: US 9,646,046 B2
(45) Date of Patent: May 9, 2017

(54) MENTAL STATE DATA TAGGING FOR DATA COLLECTED FROM MULTIPLE SOURCES

(71) Applicant: Affectiva, Inc., Boston, MA (US)

(72) Inventors: Richard Scott Sadowsky, Sturbridge, MA (US); Rana el Kaliouby, Boston, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 14/214,704

(22) Filed: Mar. 15, 2014

(65) Prior Publication Data

US 2014/0201207 A1 Jul. 17, 2014

Related U.S. Application Data

(63) Continuation-in-part of application No. 14/144,413, filed on Dec. 30, 2013, and a continuation-in-part of (Continued)

(51) Int. Cl.
*G06K 9/00* (2006.01)
*G06F 17/30* (2006.01)
(Continued)

(52) U.S. Cl.
CPC ........ *G06F 17/30386* (2013.01); *A61B 5/165* (2013.01); *G06F 19/345* (2013.01);
(Continued)

(58) Field of Classification Search
CPC ........... G06K 9/00275; G06K 9/00281; G06K 9/0028; G06K 9/00295; G06K 9/00302;
(Continued)

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.

(Continued)

*Primary Examiner* — Wesley Tucker
(74) *Attorney, Agent, or Firm* — Adams Intellex, PLC (57) ABSTRACT

Mental state data useful for determining mental state information on an individual, such as video of an individual's face, is captured. Additional data that is helpful in determining the mental state information, such as contextual information, is also determined. The data and additional data allows interpretation of individual mental state information. The additional data is tagged to the mental state data and at least some of the mental state data, along with the tagged data, can be sent to a web service where it is used to produce further mental state information.

35 Claims, 7 Drawing Sheets

Related U.S. Application Data application No. 13/153,745, filed on Jun. 6, 2011, application No. 14/214,704, which is a continuation-in-part of application No. 14/064,136, filed on Oct. 26, 2013, now Pat. No. 9,204,836, and a continuation-in-part of application No. 13/153,745, filed on Jun. 6, 2011.

(60) Provisional application No. 61/790,461, filed on Mar. 15, 2013, provisional application No. 61/793,761, filed on Mar. 15, 2013, provisional application No. 61/789,038, filed on Mar. 15, 2013, provisional application No. 61/798,731, filed on Mar. 15, 2013, provisional application No. 61/844,478, filed on Jul. 10, 2013, provisional application No. 61/916,190, filed on Dec. 14, 2013, provisional application No. 61/924,252, filed on Jan. 7, 2014, provisional application No. 61/927,481, filed on Jan. 15, 2014, provisional application No. 61/747,651, filed on Dec. 31, 2012, provisional application No. 61/747,810, filed on Dec. 31, 2012, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/719,383, filed on Oct. 27, 2012.

(51) Int. Cl.
*A61B 5/16* (2006.01)
*G06F 19/00* (2011.01)
*A61B 5/0205* (2006.01)
*A61B 5/024* (2006.01)
*A61B 5/053* (2006.01)
*A61B 5/08* (2006.01)
*A61B 5/11* (2006.01)
*G06Q 30/02* (2012.01)
*G06Q 50/00* (2012.01)

(52) U.S. Cl.
CPC ...... *G06F 19/3418* (2013.01); *G06F 19/3481* (2013.01); *A61B 5/02055* (2013.01); *A61B 5/02405* (2013.01); *A61B 5/0533* (2013.01); *A61B 5/08* (2013.01); *A61B 5/11* (2013.01); *G06Q 30/0271* (2013.01); *G06Q 50/01* (2013.01)

(58) Field of Classification Search
CPC ........... G06K 9/00308; G06K 9/00315; G06K 9/00335; G06K 9/00342; G06K 9/00348; G06K 9/00355; G06K 9/00362; G06K 9/00241
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstrom et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,676,138 A * | 10/1997 | Zawilinski .................. 600/301 |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |

(56) References Cited

U.S. PATENT DOCUMENTS

| | | |
|---|---|---|
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,401,248 B1 | 3/2013 | Moon et al. |
| 8,600,120 B2 | 12/2013 | Gonion et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1* | 11/2002 | Eshelman et al. ......... 340/573.1 |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0078513 A1 | 4/2003 | Marshall |
| 2003/0093784 A1* | 5/2003 | Dimitrova .............. H04N 7/163 725/10 |
| 2003/0191682 A1 | 10/2003 | Shepard et al. |
| 2003/0191816 A1 | 10/2003 | Landress et al. |
| 2004/0181457 A1 | 9/2004 | Biebesheimer et al. |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0115157 A1 | 6/2006 | Mori |
| 2006/0143647 A1 | 6/2006 | Bill |
| 2006/0235753 A1* | 10/2006 | Kameyama ..................... 705/15 |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0299964 A1 | 12/2007 | Wong et al. |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1* | 11/2008 | Jung .................. G06F 19/3406 600/544 |
| 2009/0006206 A1 | 1/2009 | Groe et al. |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0210290 A1 | 8/2009 | Elliott et al. |
| 2009/0217315 A1 | 8/2009 | Malik et al. |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1* | 10/2010 | Anderson et al. ............ 709/203 |
| 2011/0092780 A1 | 4/2011 | Zhang et al. |
| 2011/0126226 A1 | 5/2011 | Makhlouf |
| 2011/0143728 A1 | 6/2011 | Holopainen et al. |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0293548 A1 | 11/2012 | Perez et al. |
| 2012/0304206 A1 | 11/2012 | Roberts et al. |

FOREIGN PATENT DOCUMENTS

| | | |
|---|---|---|
| KR | 10-2008-0016303 A | 2/2008 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming HE, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

* cited by examiner

MENTAL STATE DATA TAGGING FOR DATA COLLECTED FROM MULTIPLE SOURCES

RELATED APPLICATIONS

This application claims the benefit of U.S. provisional patent applications "Mental State Data Tagging for Data Collected from Multiple Sources" Ser. No. 61/790,461, filed Mar. 15, 2013, "Mental State Analysis Using Heart Rate Collection Based on Video Imagery" Ser. No. 61/793,761, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014. This application is also a continuation-in-part of U.S. patent application "Collection of Affect Data from Multiple Mobile Devices" Ser. No. 14/144,413, filed Dec. 30, 2013, which claims the benefit of U.S. provisional patent applications "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793, 761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013 which is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011 and is also a continuation-in-part of U.S. patent application "Sporadic Collection of Mobile Affect Data" Ser. No. 14/064,136, filed Oct. 26, 2012, which claims the benefit of U.S. provisional patent applications "Sporadic Collection of Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793, 761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013 which is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to tagging of mental state data collected from multiple sources.

BACKGROUND

People spend an ever-increasing amount of time interacting with computers, and consume a vast amount of computer-delivered media. This interaction can be for many different reasons, such as a desire to find educational or entertaining content, to interact with others using social media, to create documents, and to play games, to name a few examples.

In some cases, the human-computer interaction can take the form of a person performing a task using a software-based tool running on a computer. Examples include creating a document, editing a video, and/or doing one or more of the numerous other activities a modern computer can perform. The person might find the execution of certain activities interesting or even exciting, and might be surprised at how easy it is to perform the activity. The person can become excited, happy, or content as he or she performs an interesting or exciting activity. On the other hand, the person might find some activities difficult to perform, and might become frustrated or even angry with the computer or software tool. In some cases, for example, users are surveyed in an attempt to determine whether or not a computer or computer program functioned well and to identify where the computer program might need improvement. However, such survey results are often unreliable because the surveys are often completed well after the activity was performed. In addition, survey participation rates can be low, and people may not provide accurate and honest answers to the survey.

In other cases of human-computer interaction, a person might not be using a software tool to accomplish a task, but instead might be consuming computer-accessed content or media such as news, pictures, music, or video. Currently, people consuming computer-driven content can tediously self-rate the media if they wish to communicate personal preferences. In some cases, viewers enter a specific number of stars corresponding to a level of like or dislike, while in other cases, users are asked to answer a list of questions. While a system for collecting users' evaluations of media and other products or services can be a helpful metric, current evaluation schemes are often tedious and challenging. Recommendations based on such a system of star rating and/or other means of self-reporting are imprecise, subjective, unreliable, and are further limited by sample size, as only a small number of viewers prove to actually rate the media they consume. Thus, in many cases, such subjective evaluation is neither a reliable nor practical way to evaluate personal responses to media.

A third-party observer can also be used to evaluate the human-computer interaction. A trained observer can often infer the user's mental state simply by observing the individual, their actions, and their context—e.g. their environment. The third party might also interact with the user and ask them questions about how they are feeling or details about what they are doing. While such a methodology can provide interesting results, the need for a trained observer to view and analyze the user means that using third-party observers is not scalable to large numbers of people performing many tasks in many locations. It also might be possible that the mere presence of the observer impacts the user's mental state, generating questionable results.

SUMMARY

Mental state data, such as video of an individual's face, is captured on the individual and is useful for determining mental state information on that individual. Additional data is also determined that is helpful in determining the mental state information, helps to interpret the mental state information, or otherwise provides information about mental states. The additional data is tagged to the mental state data and at least some of the mental state data is sent to a web service where it may be used to produce mental state information. A computer-implemented method for mental state analysis is disclosed comprising: receiving two or more portions of mental state data tagged with additional information; selecting one or more portions of the received two or more portions of mental state data based on the additional information that was tagged; and analyzing the one or more selected portions of mental state data to generate mental state information wherein a result from the analyzing is used to render an output on mental states. The one or more portions of mental state data may be selected based, at least in part, on tags identifying a particular individual. The one or more portions of mental state data may be selected based, at least in part, on tags identifying a particular context.

In embodiments, a computer-implemented method for mental state analysis comprises: capturing mental state data on an individual from a first source; determining additional data about the mental state data wherein the additional data provides information about mental states; tagging the additional data to the mental state data; and sending at least a portion of the mental state data tagged with the additional data to a web service. The context may comprise an identity of another person in proximity of the individual.

In some embodiments, a computer-implemented method for mental state analysis comprises: receiving an analysis based on both mental state data and additional data tagged to the mental state data; and rendering an output based on the analysis. In some embodiments, a computer-implemented method for mental state analysis comprises: obtaining mental state data which is collected on an individual from multiple sources; determining a portion of the mental state data that is to be sent to a web service; determining additional data about the mental state data; tagging the additional data to the portion that is to be sent to the web service; analyzing the mental state data from multiple sources using the additional data that was tagged; and rendering an output about mental states based on the mental state data on the individual from multiple sources along with the additional data that was tagged. In embodiments, a computer program product embodied in a non-transitory computer readable medium for mental state analysis comprises: code for capturing mental state data on an individual from a first source; code for determining additional data about the mental state data wherein the additional data provides information about mental states; code for tagging the additional data to the mental state data; and code for sending at least a portion of the mental state data tagged with the additional data to a web service. In some embodiments, a computer system for mental state analysis comprises: a memory which stores instructions; one or more processors attached to the memory wherein the one or more processors, when executing the instructions which are stored, are configured to: capture mental state data on an individual from a first source; determine additional data about the mental state data wherein the additional data provides information about mental states; tag the additional data to the mental state data; and send at least a portion of the mental state data tagged with the additional data to a web service.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

As a user interacts with a computing device, the user's mental state can provide valuable insight into the nature of the human-computer interaction. The mental state of the user can include such emotions as frustration, confusion, disappointment, hesitation, cognitive overload, fear, exhaustion, focus, engagement, attention, boredom, exploration, confidence, trust, delight, satisfaction, excitement, happiness, contentment, or many other human emotions. Understanding a user's mental state as he or she interacts with the computing device can prove valuable for a variety of reasons, including determining which aspects of a computer program are working well and which aspects need improvement; determining aspects of a computer game that are too difficult for some users or too easy for some users; measuring the effectiveness of advertisements; determining which parts of a video most please a specific user; or determining a user's preferences in order to better suggest what other media, games, or applications the specific user finds appealing, among other potential reasons.

While consuming media, the user can exhibit physical manifestations of his or her mental state, such as facial expressions, physiological reactions, and movements. Sensors coupled to a computer—depending on the embodiment, either the same computer with which the user is interacting or one or more other computers—can detect, capture, and/or measure one or more external manifestations of the user's mental state. In embodiments, for example, a still camera can capture images of the user's face; a video camera can capture images of the user's movements; a heart rate monitor can measure the user's heart rate; a skin conductance sensor can detect changes in the user's electrodermal activity response; and an accelerometer can measure such movements as gestures, foot tapping, or head tilts. Many other sensors and capabilities are possible. Some embodiments include multiple sensors to capture the user's mental state data.

Other data related to the mental state data can be determined; the identity of the individual being monitored, for example. Additionally, the task that the individual is performing or the media that the user is consuming can be identified, among other data points. A time, date, and/or location can be logged and surrounding environmental data such as temperature, humidity, lighting levels, noise levels, and the like, can be determined. Any number of other factors can be determined and tagged to the mental state data in order to associate the additional data with the mental state data. Tagging the additional data to the mental state data can be performed by including the additional data in the file that holds the mental state data. Any format can be used for the additional data, depending on file format used for the mental state data. Some examples of formats that can be used for the additional data include, but are not limited to, ID3, exchangeable image file format (EXIF), extensible metadata platform (XMP), or other metadata standards. By tagging the mental state data with the additional data, the additional data is persistently associated with the mental state data.

Once the mental state data has been collected and tagged with the additional data, at least some of the tagged mental state data is sent to a web service. The web service can comprise a computer that is communicated with over a network or through a network of networks, such as the internet. The web service receives the tagged mental state data and selects some of the tagged mental state data based on the additional data included in the tags. The web service then analyzes the selected tagged mental state data to create mental state information about the individual. The mental state information is then used, either by the web service or by another computer that receives the mental state information from the web service, to render an output. In some embodiments, the rendering is performed on the computer hosting the web service, while in other embodiments, the rendering is either executed on the computer that originally collected the mental state data or on a different computer.

The rendered output can include text, icons, pictures, graphs, binary data, or any other form or output that, depending on the embodiment, can be interpreted by a person or another computer. In at least one embodiment, the rendered output includes a graph showing the prevalence of a particular mental state over time. In some embodiments, the rendered output includes an icon that changes based on the user's mental state. In some embodiments, the rendered output includes a file containing numerical data based on the obtained analysis. The result of the mental state analysis can also be included in a calendar where it can be displayed or compared with the ongoing activities already included in the calendar.

Figure 1:
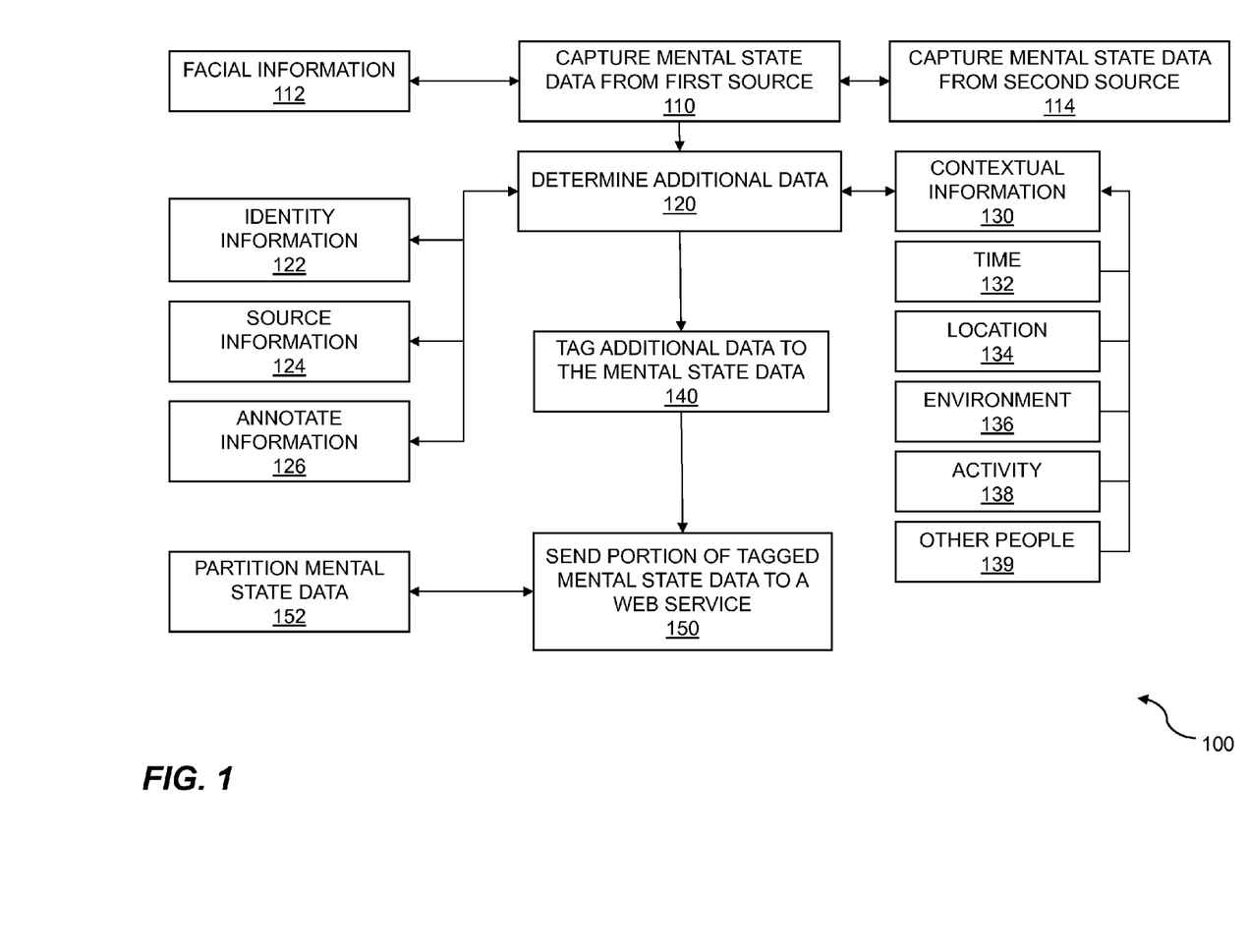
FIG. 1 is a flow diagram for mental state analysis.

FIG. 1 is a flow diagram 100 for mental state analysis. The flow 100 describes a computer-implemented method for mental state analysis that includes capturing mental state data on an individual from a first source 110. The mental state data includes still images or video of the individual in some embodiments; these images or video can include the individual's face. Thus, the mental state data from the first source can include facial information 112. In some embodiments, the mental state data includes data from biosensors or other types of mental state data. The flow 100 comprises, in some embodiments, obtaining mental state data from a second source 114 where the mental state data from the second source can include facial information.

The flow 100 also includes determining additional data 120 about the mental state data. The additional data can be information about the identity 122 of the individual, information about the source 124 of the mental state data, contextual information 130, or other metadata. In other words, the additional data can include information on a source 124 that collected the mental state data, and/or the context 130 in which the mental state data was collected. In some embodiments, the context comprises a time 132, while in other embodiments the context comprises a location 134. The location can be determined by any mechanism including, but not limited to, internet protocol (IP) address mapping, manual entering of location data by an operator or the individual being monitored, or by receiving radio broadcasts. In at least one embodiment, the location is determined using GPS. The location can be identified using any type of identification including, but not limited to, an address, latitude and longitude coordinates, a building identifier, or a room identifier. Practically, the location information could identify a building, a room, or another type of address or position. Additionally, in some embodiments the context comprises environmental information 136.

In many embodiments, the context comprises an activity 138 performed by the individual. The activity includes at least one of talking on a phone, playing a videogame, working at a computer, or watching a media presentation, depending on the embodiment. The context can further include information further identifying the context, such as the name or number of the other party on the phone, the name of the videogame, a descriptor of the activity being performed within the videogame, the type of activity being worked on with the computer, the name of the media presentation being watched, or other information. In other embodiments, the context comprises an identity for another person or other people 139 within a given proximity of the individual. The additional data can include human coded information on the individual. The additional data can be annotated information 126 using the human coded information. The human coded information can include analysis of mental states seen by the human coder in the face of the individual. The human coded information can include a summary of the mental state analysis.

The additional data can include information about an identity of the individual 122. The information about the individual can be in any form, but in some embodiments the information about the identity of the individual includes a name of the individual and/or an identity value for the individual. The identity of the individual can be determined by any method, including, but not limited to, manual entry by the individual or an operator, a computer system account login, or an identity card scan. In at least one embodiment, the information about the identity of the individual is determined using face recognition.

The various data and additional data from multiple sources can be synchronized. In some embodiments, the data and additional data can include timestamps for synchronizing. In other cases some repetitive pulse can be used to align information as needed which can, in some cases, be an audio or light pulse or group of pulses. These pulses can be used for later alignment of the data and additional data during analysis.

The flow 100 includes tagging the additional data to the mental state data 140. Through such tagging, additional data can be associated with the mental state data. The tagging can be done by any method for associating data in a computer system. By tagging the mental state data with the additional data, the additional data is associated with the mental state data in a persistent manner. In some embodiments, the additional data can be included in the file that holds the mental state data. Depending on file format used for the mental state data, any format can be used for the additional data. Some examples of formats that can be used for the additional data include ID3, exchangeable image file format (EXIF), extensible metadata platform (XMP), or any other metadata standard. In other embodiments, the additional data is stored in a separate file linked to the file that holds the mental state data. In yet other embodiments, a separate file contains links to both the additional data file and the mental state data file.

The flow 100 includes sending at least a portion of the mental state data tagged with the additional data to a web service 150. The web service can be contacted over a network or a network of networks—such as the Internet— and the web service can be hosted on a different computer than the computer used to capture the mental state data. The mental state data can be partitioned 152 based on the additional data. The portion of the mental state data to be sent to the web service can be determined based on the additional data. In one embodiment, the tagged mental state data is examined and the portions which are tagged with the identity of a particular individual are sent. In other embodiments, the portions that are tagged with a particular activity are sent. Other embodiments utilize different tags to determine the portions of the mental state date to be sent. In at least one embodiment, the portion of the mental state data to be sent to the web service is determined based on facial recognition performed on the mental state data when the mental state data is comprised of facial images. The mental state data can be combined with data from other sources, such as social media information, to augment the mental state analysis. In some cases a user can obtain feedback based on the mental state data in order to enhance an experience for the user.

The flow 100 can further comprise analyzing the mental state data to produce mental state information. In some embodiments, the analyzing is performed based on facial movement. Other embodiments analyze biosensor data to produce mental state information. Various mental states can be inferred, such as frustration, confusion, disappointment, hesitation, cognitive overload, fear, exhaustion, focus, engagement, attention, boredom, exploration, confidence, trust, delight, satisfaction, excitement, happiness, sadness, stress, anger, contentment, or many other human emotions. In some embodiments, the additional data is used in conjunction with the mental state data to produce the mental state information. In some embodiments, the additional data is used to limit the mental state data that is analyzed. In other embodiments, the additional data directly contributes to the determining of the mental state, such as by analyzing the contents of an email being read. Various steps in the flow 100 may be changed in order, repeated, omitted or the like without departing from the disclosed concepts. Various embodiments of the flow 100 may be included in a computer program product embodied in a non-transitory computer readable medium that includes code executable by one or more processors.

Figure 2:
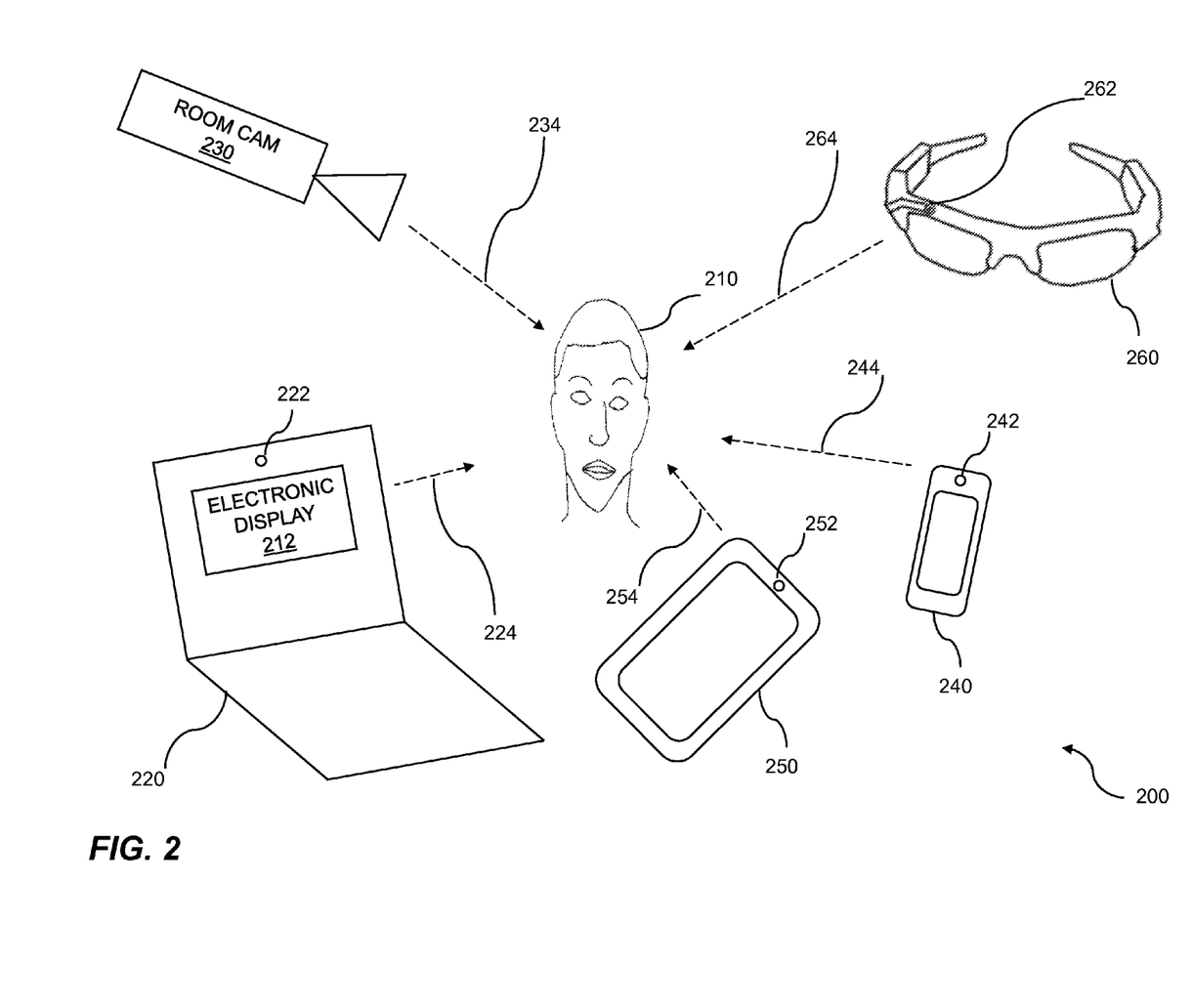
FIG. 2 is a diagram showing facial data collection from multiple devices.

FIG. 2 is a diagram 200 showing facial data collection from multiple devices. The facial data collected from the plurality of sources can be mental state data. A user 210 can be performing a task, viewing a media presentation on an electronic display 212, or doing any activity where it can be useful to determine the user's mental state. The electronic display 212 can be on a laptop computer 220 as shown, a tablet computer 250, a cell phone 240, a desktop computer monitor, a television, or any other type of electronic device. The mental state data can be collected on a mobile device such as a cell phone 240, a tablet computer 250, or a laptop computer 220; a fixed device, such as the room camera 230; or a wearable device, such as glasses 260. Thus, the plurality of sources can include at least one mobile device such as a phone 240 or a tablet 250, or a wearable device such as glasses 260. A mobile device can include a forward facing camera and/or rear facing camera which can be used to collect mental state data. The plurality of sources of facial data can include one or more of a webcam 222, a phone camera 242, a tablet camera 252, and a wearable camera 262.

As the user 210 is monitored, the user 210 can move due to the nature of the task, boredom, distractions, or for another reason. As the user moves, the user's face can be visible from one or more of the multiple sources. In some embodiments, for example, if the user 210 is looking in a first direction, the line of sight 224 from the webcam 222 can observe the individual's face, but if the user is looking in a second direction, the line of sight 234 from the room camera 230 can observe the individual's face. Further, if the user is looking in a third direction, the line of sight 244 from the phone camera 242 can observe the individual's face. If the user is looking in a fourth direction, the line of sight 254 from the tablet cam 252 can observe the individual's face. If the user is looking in a fifth direction, the line of sight 264 from the wearable camera 262 can observe the individual's face. The wearable device, such as the glasses 260, can be worn by another user or an observer. In other embodiments, the wearable device is a device other than glasses, such as an earpiece with a camera, a helmet or hat with a camera, a clip-on camera attached to clothing, or any other type of wearable device with a camera or other sensor for collecting mental state data. The individual 210 can also wear a wearable device including a camera which can be used for gathering contextual information and/or collecting mental state data on other users. Because the individual 210 can move his or her head, the facial data can be collected intermittently when the individual is looking in a direction of a camera. In some cases, multiple people are included in the view from one or more cameras, and some embodiments include filtering out faces of one or more other people to determine whether the individual 210 is looking toward a camera.

Figure 3:
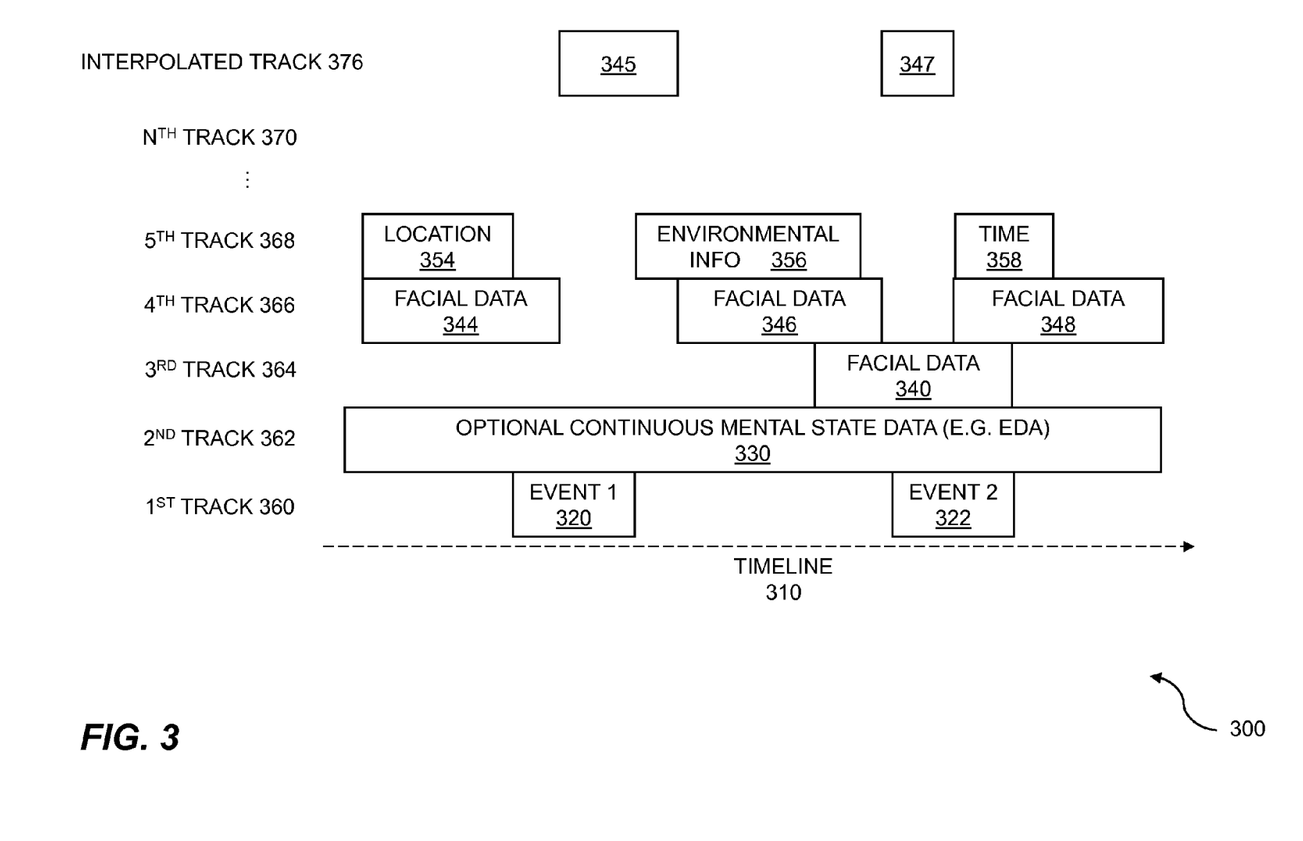
FIG. 3 is a timeline with information tracks relating to mental states.

FIG. 3 is a timeline 310 with information tracks 300 relating to mental states. A first track 360 shows events which can be related to the individual's use of a computer. A first event 320 marker can indicate an action that the individual took (such as launching an application); an action initiated by the computer (such as the presentation of a dialog box); an external event (such as a new global positioning system [GPS] coordinate); or an event such as the receipt of an e-mail, a phone call, a text message, or the like. In some embodiments, a photograph can be used to document an event or simply save contextual information in the first track 360. A second event 322 marker can indicate another action or event. Such event markers can be used to provide contextual information and can also include such things as copies of emails, text messages, phone logs, file names, or other information that can prove useful in understanding the context of a user's actions.

A second track 362 can include continuously collected mental state data such as electrodermal activity data 330. A third track 364 can include facial data 340, which can be collected on an intermittent or continuous basis by a first camera, such as the room camera 230 of FIG. 2. Thus, the mental state data from the first source can include facial information. The facial data can be collected intermittently when the individual is looking toward a camera. The facial data 340 can include one or more still photographs, videos, or abstracted facial expressions which can be collected when the user looks in the direction of the camera. A fourth track 366 can include facial data collected on an intermittent or continuous basis by a second camera, such as the mobile phone cam 242 of FIG. 2. The fourth track can include three instances of collected facial data 344, 346, and 348. The three collected instances of facial data 344, 346, and 348 can include one or more still photographs, videos, or abstracted facial expressions which can be collected when the user looks in the direction of a camera.

A fifth track 368 can include contextual data collected simultaneously with the mental state data. In one example, the fifth track 368 includes location data 354, environmental information 356, and time data 358, although other contextual data can be collected in other embodiments. In the embodiment shown, the fifth track 368 of contextual data can be associated with the fourth track 366 of mental state data. Some embodiments determine multiple tracks of additional data that can be associated with one or more tracks of mental state data. For example, another track can include identity information of the individual being monitored by the camera capturing the third track 364 of mental state data.

Additional tracks—in the timeline shown, through the nth track 370—of mental state data or additional data of any type can be collected. The additional tracks can be collected on a continuous or on an intermittent basis. The intermittent basis can be either occasional or periodic. Analysis can further comprise interpolating mental state data when the collected mental state data is intermittent, and/or imputing additional mental state data where the mental state data is missing. One or more interpolated tracks 372 can be included and can be associated with mental state data that is collected on an intermittent basis, such as the facial data of the fourth track 366. The two instances of interpolated data, interpolated data 345 and interpolated data 347, can contain interpolations of the facial data of the fourth track 366 for the time periods where no facial data was collected in that track. Other embodiments interpolate data for periods where no track includes facial data. In other embodiments, analysis includes interpolating mental state analysis when the collected mental state data is intermittent.

The mental state data, such as the continuous mental state data 330 and/or any of the collected facial data can be tagged. In the example timeline shown, facial data 340, 344, 346, and 348 are tagged. The tags can include metadata related to the mental state data, including, but not limited to, the device that collected the mental state data; the individual from whom the mental state data was collected; the task being performed by the individual; the media being viewed by the individual; and the location, the environmental conditions, the time, the date, or any other contextual information useful for mental state analysis. The tags can be used to locate pertinent mental state data; for example, the tags can be used to identify useful mental state data for retrieval from a database. The tags can be included with the mental state data that is sent over the internet to cloud or web-based storage and/or services and can be used remotely, but the tags can also be used locally on the machine where the mental state data was collected.

Figure 4:
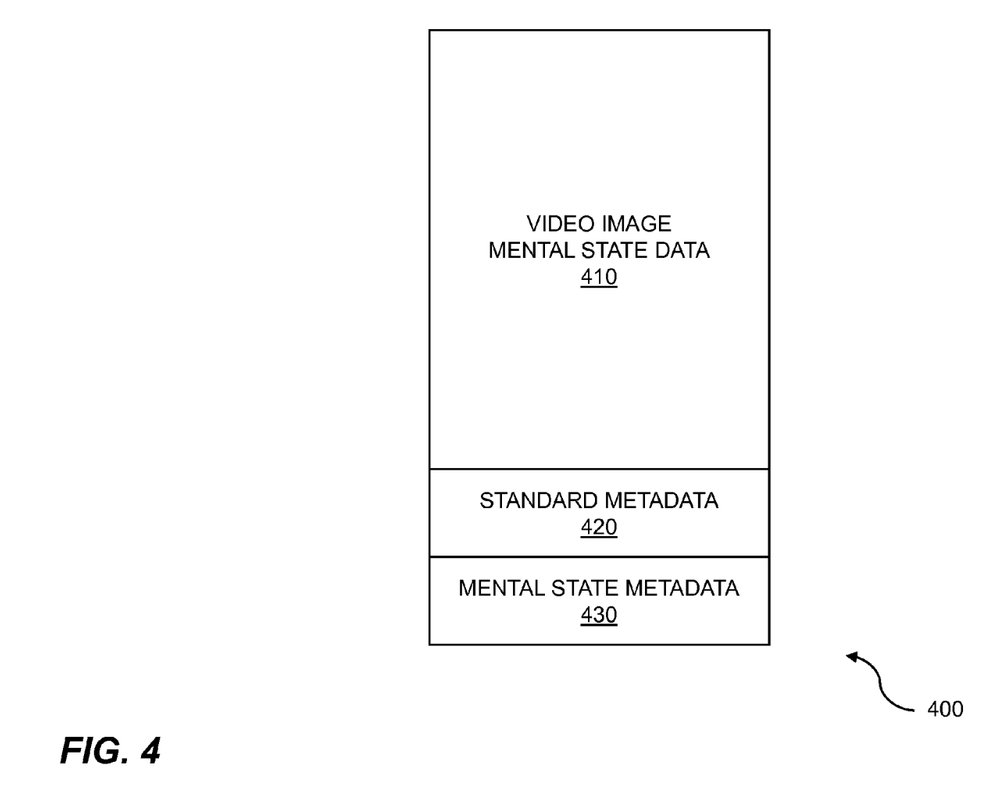
FIG. 4 shows mental state data with tags.

FIG. 4 shows mental state data with tags 400. The mental state data with tags 400 includes video image mental state data 410 captured on an individual from a first source. In some embodiments, the source of the mental state data includes certain standard metadata 420 with the mental state data 410. For example, a video camera which includes timestamps along with video data demonstrates such metadata inclusion. A still camera which includes EXIF data identifying the camera model, exposure information, and day and date information in the JPEG file containing the compressed image data shows another instance of metadata inclusion.

In embodiments, additional data which provides information about the mental state data 410 is determined. Such additional data can be tagged to the mental state data as mental state metadata 430. The mental state metadata 430 can provide information about the mental states useful in the analysis of the mental state data 410. The mental state metadata 430, or additional data, is data that is not tagged to the mental state data by the source of the mental state data and not always known to the source of the mental state data 410. Thus, the mental state metadata 430 is tagged to the mental state data 410 by an entity that is not the original source of the mental state data.

In one embodiment, a video camera is used to capture the mental state data 410. The video camera can include standard metadata 420 such as time and date and model number of the camera, along with the video image, which in this case comprises video image mental state data 410, in a MPEG-4 data stream that is sent from the video camera to a mental state collection machine. The standard metadata 420 can be included using standard metadata formats defined by the MPEG-4 specification. The mental state collection machine can determine an identity of the individual being monitored, such as a login ID, and an activity of that individual, such as watching a particular media presentation. The mental state collection machine can then tag the video image with the login ID and the name of the particular media presentation as mental state metadata 430. In at least one embodiment, the mental state collection machine formats the mental state metadata as XMP metadata and includes it in the MPEG-4 file. Other embodiments determine different additional information to be used as mental state metadata 430 and use different formats to tag the mental state data 410 with the mental state metadata 430.

Once the data collection machine has captured mental state data, at least a portion of the mental state data tagged with the additional data is sent to a web service. The portion of the mental state data sent to the web service can be based on the additional data, or can be based on mental state metadata 430. At the web service, portions of mental state data can be selected for analysis based, at least in part, on tags identifying one or more contexts. In at least one embodiment, the selected portions are based, at least in part, on identifying a particular individual. In some embodiments, the selected portions include tags identifying at least two different timestamps so that samples can be distributed over a period of time. In at some embodiments, the selected portions are based, at least in part, on tags identifying a particular context. Once the portions are selected, they can be analyzed by the web service and used to create mental state information.

Figure 5:
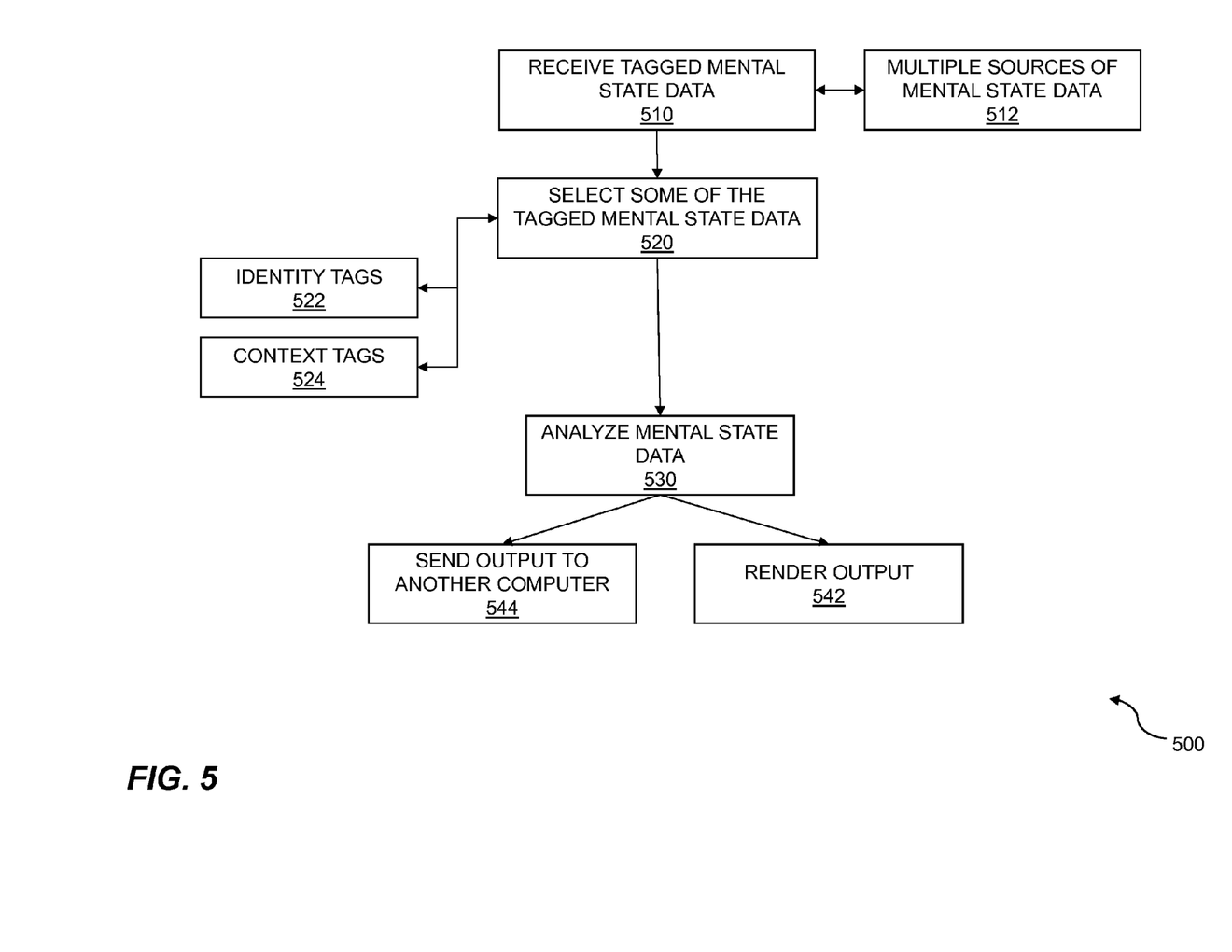
FIG. 5 is a flow diagram for mental state analysis.

FIG. 5 is a flow diagram 500 for mental state analysis. The flow 500 describes a computer-implemented method for mental state analysis where tagged mental state data is received. The flow 500 includes receiving two or more portions of mental state data tagged with additional information 510. In some embodiments, the mental state data is received from multiple sources 512, so the two or more portions can come from a plurality of sources of facial data. In some cases analysis can be performed to evaluate mental state data measurements across various devices from which the mental state data is received. The flow 500 continues by selecting one or more portions of the received two or more portions of mental state data 520, based on the additional data from the tags. In some embodiments, the one or more portions of mental state data are selected based, at least in part, on tags identifying a particular individual 522, or the one or more portions of mental state data can be selected based, at least in part, on tags identifying one or more contexts 524. Context information can be used to focus on an area of analysis. Likewise, context information can be used to exclude certain events from mental state analysis. For instance, any mental state data associated with unintended noise or distraction can be tagged to be ignored during later analysis. In some embodiments, the one or more portions of mental state data are selected to include tags identifying at least two different timestamps. The one or more portions of mental state data can be selected based, at least in part, on tags identifying a particular context comprising a particular location, a particular activity, or the like. Any algorithm can be used to select the one or more portions for analysis.

The flow 500 continues by analyzing the one or more selected portions of mental state data 530 to generate mental state information wherein a result from the analyzing is used to render an output on mental states 542. Analysis and rendering, based on tagged data, can aid a human user in being able to focus on areas of particular interests without wading through enormous sums of irrelevant data. A rendering can include a summary of mental states, a graphical display showing a media presentation and associated mental states, a social media pages with mental state information, and the like. The rendering can also include excerpts of a media presentation such as, in some embodiments, a highlight-reel style presentation based on mental states and associated tagged data. In some cases portions of a media presentation can be excluded based on mental states and tagged data. In some embodiments, the same computer that was used to analyze the mental state data 530 is also used to render the output, but in other embodiments, the output used for rendering being sent to another computer 544 where the other computer provides the rendering. The rendering can be any type of rendering including textual rendering, graphical rendering, pictorial rendering, or a combination thereof. In some embodiments, another computer can provide information to another user. This other user can perform various analyses including A/B type testing and comparisons. Various steps in the flow 500 may be changed in order, repeated, omitted, or the like without departing from the disclosed concepts. Various embodiments of the flow 500 may be included in a computer program product embodied in a non-transitory computer readable medium that includes code executable by one or more processors.

Figure 6:
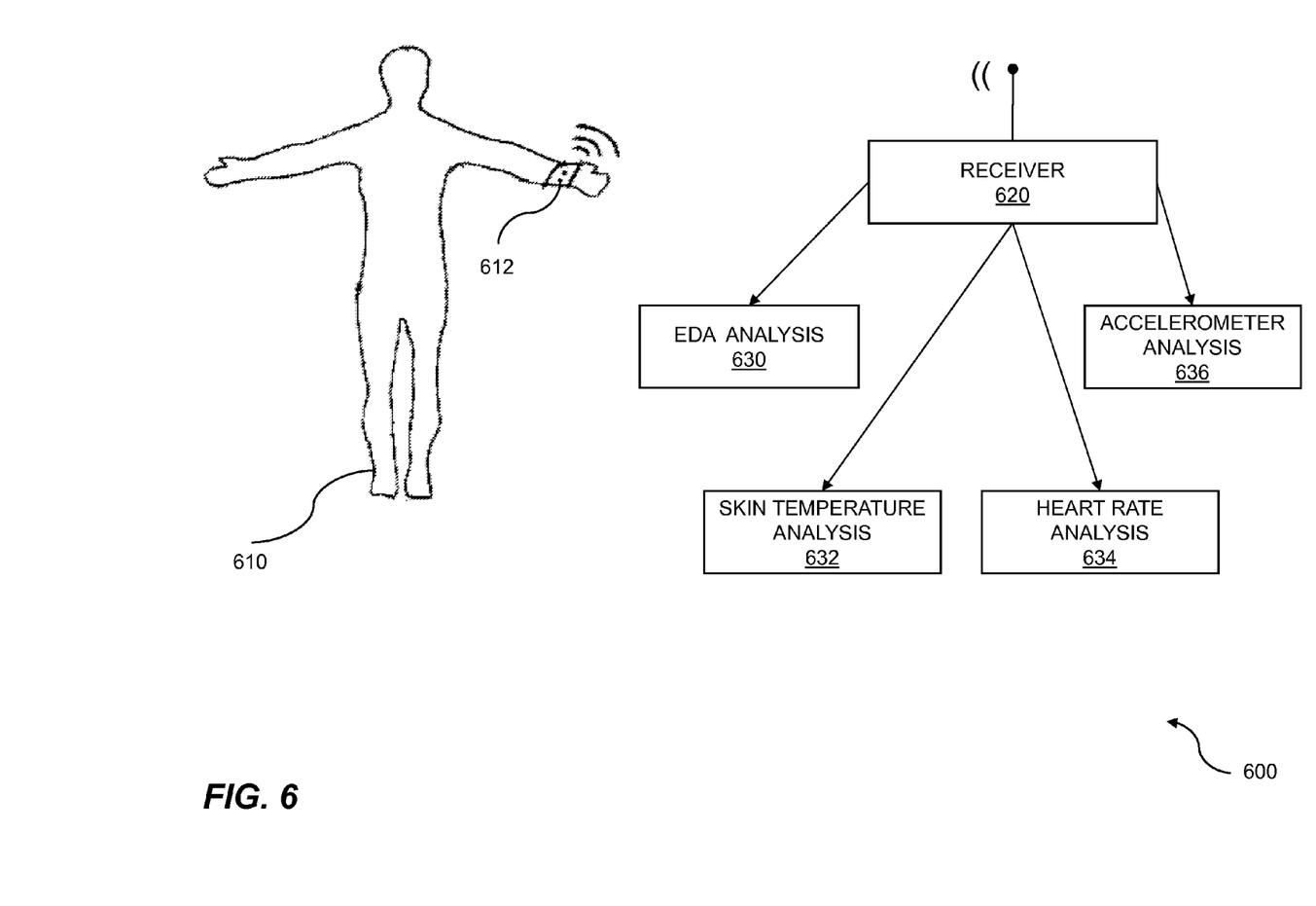
FIG. 6 is a diagram for sensor analysis.

FIG. 6 is a diagram for sensor analysis. A system 600 can analyze data collected from a person 610 as he or she interacts with a computer or views a media presentation. The person 610 can have a biosensor 612 attached to him or her for the purpose of collecting mental state data and biosensor information. The biosensor 612 can be placed on the wrist, palm, hand, head, or another part of the body. In some embodiments, multiple biosensors are placed on the body in multiple locations. The biosensor 612 can include detectors for physiological data such as electrodermal activity, skin temperature, accelerometer readings, and the like. Other detectors for physiological data can also be included, such as heart rate, blood pressure, EKG, EEG, other types of brain waves, and other physiological detectors. The biosensor 612 can transmit collected information to a receiver 620 using wireless technology such as Wi-Fi, Bluetooth®, 802.11, cellular, or other bands. In other embodiments, the biosensor 612 communicates with the receiver 620 using other methods such as a wired or optical interface. The receiver can provide the collected data to one or more components in the system 600. In some embodiments, the biosensor 612 records multiple types of physiological information in memory for later download and analysis. In some embodiments, the download of recorded physiological data is accomplished through a USB port or another form of wired or wireless connection.

Mental states can be inferred based on physiological data such as the physiological data from the sensor 612. Mental states can also be inferred based on facial expressions and head gestures observed by a webcam, or by using a combination of data from the webcam and data from the sensor 612. The mental states can be analyzed based on arousal and valence. Arousal can range from being highly activated, such as when someone is agitated, to being entirely passive, such as when someone is bored. Valence can range from being very positive, such as when someone is happy, to being very negative, such as when someone is angry. Physiological data can include one or more of electrodermal activity (EDA), heart rate, heart rate variability, skin temperature, respiration, accelerometer readings, and other types of analysis of a human being. It should be understood that both here and elsewhere in this document, physiological information can be obtained either by biosensor 612 or by facial observation via an image capturing device. Facial data can include facial actions and head gestures used to infer mental states. Further, the data can include information on hand gestures, body language, and body movements such as visible fidgets. In some embodiments, these movements are captured by cameras, while in other embodiments, these movements are captured by sensors. Facial data can include tilting of the head to the side, leaning forward, smiling, frowning, and many other gestures or expressions.

In some embodiments, electrodermal activity is collected, either continuously, every second, four times per second, eight times per second, 32 times per second, or on some other periodic basis. Alternatively, electrodermal activity can be collected on an intermittent basis. The electrodermal activity can be recorded and stored onto a disk, a tape, flash memory, or a computer system, or can be streamed to a server. The electrodermal activity can be analyzed 630 to indicate arousal, excitement, boredom, or other mental states based on observed changes in skin conductance. Skin temperature can be collected and/or recorded on a periodic basis. In turn, the skin temperature can be analyzed 632. Changes in skin temperature can indicate arousal, excitement, boredom, or other mental states. Heart rate information can also be collected, recorded, and analyzed 634. A high heart rate can indicate excitement, arousal, or other mental states. Accelerometer data can be collected and used to track one, two, or three dimensions of motion. The accelerometer data can be recorded. The accelerometer data can be used to create an actigraph showing an individual's activity level over time. The accelerometer data can be analyzed 636 and can indicate a sleep pattern, a state of high activity, a state of lethargy, or other states. The various data collected by the biosensor 612 can be used along with the facial data captured by the webcam in the analysis of mental state. Contextual information can be based on one or more of skin temperature and accelerometer data. The mental state data can include one or more of a group including physiological data, facial data, and accelerometer data.

Figure 7:
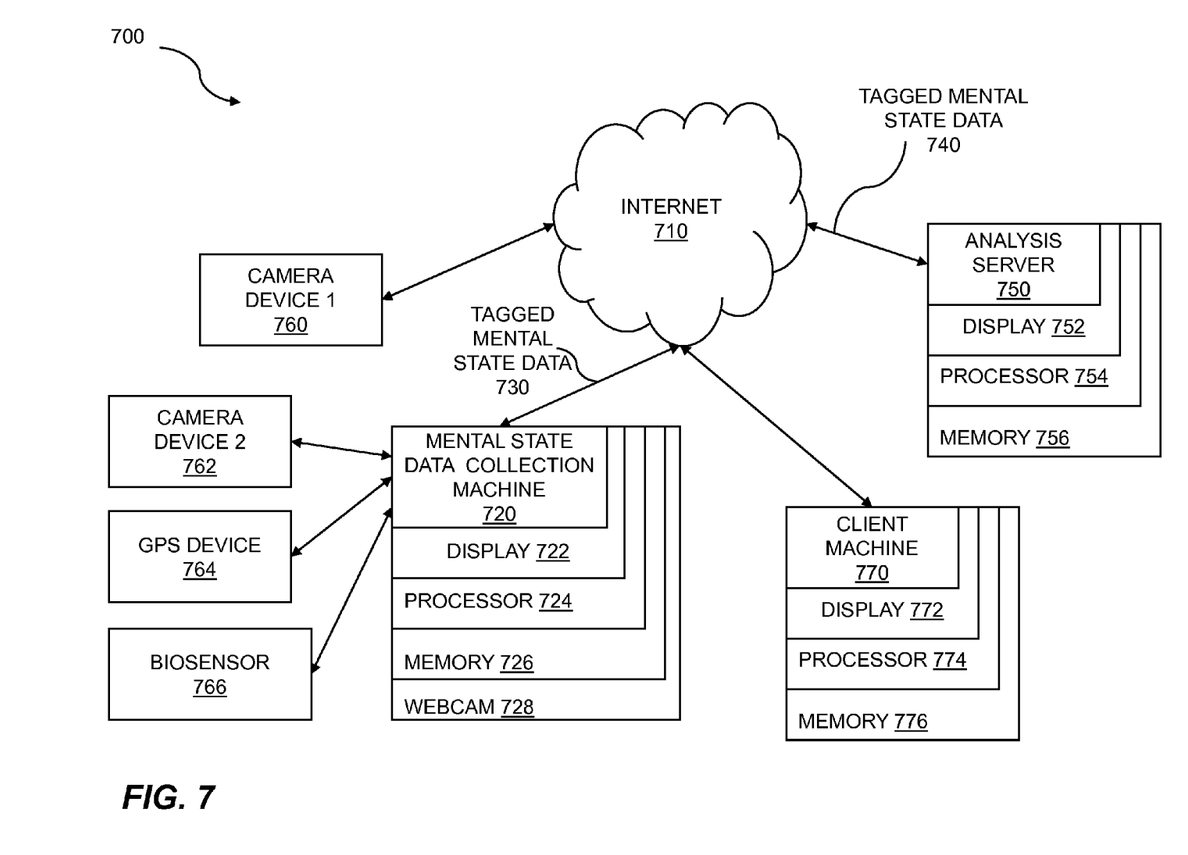
FIG. 7 is a system diagram for mental state analysis.

FIG. 7 is a system diagram for mental state analysis. The system 700 can include one or more computers coupled together by a communication link such as the Internet 710 and can be used for a computer-implemented method for mental state analysis. The system 700 can also include two or more cameras that can be linked to the one or more computers and/or directly to a communication link. The system 700 can include a mental state collection machine 720, which is referred to as a client machine in some embodiments. The mental state collection machine 720 includes a memory 726 which stores instructions, one or more processors 724 coupled to the memory, a display 722, and, in some embodiments, a webcam 728. The display 722 can be any electronic display, including but not limited to, a computer display, a laptop screen, a net-book screen, a tablet screen, a cell phone display, a mobile device display, a remote with a display, a television, a projector, or the like. The webcam 728, as the term is used herein, can refer to a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, multiple webcams used to capture different views of viewers, or any other type of image capture apparatus that allows image data captured to be used by an electronic system. In some embodiments, a second camera device 762, a GPS device 764, and/or a biosensor 766 can be coupled to the mental state collection machine 720. The second camera device 762 and/or the webcam 728 can be used to capture facial images of an individual that can be used as mental state data. Likewise, the biosensor 766 can capture mental state data from the individual. The GPS device 764 can be used to obtain location data which can then be used to provide contextual information about the mental state data. Other sensors or programs running on the mental state collection machine can be used to gather additional data relating to the mental state data.

The individual can interact with the mental state collection machine 720, interact with another computer, view a media presentation on another electronic display, and/or perform numerous other activities. The system 700 can include a computer program product embodied in a non-transitory computer readable medium including code for capturing mental state data on an individual from a first source, code for determining additional data about the mental state data wherein the additional data provides information about mental states, code for tagging the additional data to the mental state data, and code for sending at least a portion of the mental state data tagged with the additional data 730 to a web service. With such a program stored in memory, the one or more processors 724 can be configured to capture mental state data on an individual from a first source, determine additional data about the mental state data wherein the additional data provides information about mental states, tag the additional data to the mental state data, and send to a web service at least a portion of the mental state data 730 tagged with the additional data. In some embodiments, the second camera device 762 can be used as a second source of mental state data which is tagged with the additional data and sent to the web service.

Some embodiments can include an analysis server 750. In embodiments, the analysis server 750 can be configured as a web service. The analysis server 750 includes one or more processors 754 coupled to a memory 756 to store instructions. Some embodiments of the analysis server 750 include a display 752. The one or more processors 754 can be configured to receive tagged mental state data 740 from the mental state collection machine 720, the first camera device 760, and/or any other computers configured to collect mental state data. The one or more processors 754 can then select one or more portions of the received mental state data 740 based on the additional data from the tags, and can then analyze the received mental state data 740. The analysis can produce mental state information, inferred mental states, emotigraphs, actigraphs, other textual/graphical representations, or any other type of analysis. The analysis server 750 can display at least some of the analysis on the display 752 and/or can provide the analysis of the mental state data to a client machine, such as the mental state data collection machine 720, or another client machine 770, so that the analysis can be displayed to a user. The analysis server 750 can enable a method that includes receiving two or more portions of mental state data tagged with additional information, selecting one or more portions of the received two or more portions of mental state data based on the additional data from the tags, and analyzing the one or more selected portions of mental state data to generate mental state information wherein a result from the analyzing is used to render an output on mental states.

Some embodiments include another client machine 770. The client machine includes one or more processors 774 coupled to memory 776 to store instructions, and a display 772. The client machine can receive the analysis of the mental state data from the analysis server 750 and can render an output to the display 772. The system 700 can enable a computer-implemented method for mental state analysis that includes receiving an analysis based on both mental state data and additional data tagged to the mental state data, and rendering an output based on the analysis. In at least one embodiment the mental state data collection machine, the analysis server, and/or the client machine functions are accomplished by one computer.

Thus, the system 700 can enable a method including obtaining mental state data which is collected on an individual from multiple sources, determining a portion of the mental state data that is to be sent to a web service, determining additional data about the mental state data, tagging the additional data to the portion that is to be sent to the web service, analyzing the mental state data from multiple sources using the additional data that was tagged, and rendering an output about mental states based on the mental state data on the individual from multiple sources along with the additional data that was tagged.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
   receiving two or more portions of mental state data tagged with additional information, wherein the two or more portions of mental state data come from a plurality of sources of facial data, wherein the mental state data collected is intermittent, and wherein the plurality of sources includes at least one mobile device, including a cell phone, a tablet computer, a wearable device, or a laptop computer;
   interpolating the intermittent mental state data, wherein the interpolating is based on the additional information that was tagged;
   selecting one or more portions of the received two or more portions of mental state data based on the additional information that was tagged, wherein the one or more selected portions of mental state data are selected based, at least in part, on tags identifying a particular context; and analyzing, using one or more processors, the one or more selected portions of mental state data to generate mental state information wherein a result from the analyzing is used to render an output on mental states.

2. The method of claim 1 wherein the plurality of sources of facial data include one or more of a webcam, a phone camera, a tablet camera, or a wearable camera.

3. The method of claim 1 wherein the one or more selected portions of mental state data are selected based, at least in part, on tags identifying a particular individual.

4. The method of claim 3 wherein the one or more selected portions of mental state data are selected based, at least in part, on tags identifying one or more contexts.

5. The method of claim 3 wherein the one or more selected portions of mental state data are selected to include tags identifying at least two different timestamps.

6. The method of claim 1 further comprising the output used for rendering being sent to another computer and the other computer provides the rendering.

7. A computer-implemented method for mental state analysis comprising:
    capturing mental state data on an individual from a first source that includes facial information, wherein the mental state data collected is intermittent;
    capturing mental state data on the individual from at least a second source that includes facial data, wherein the at least a second source comprises a mobile device, including a cell phone, a tablet computer, a wearable device, or a laptop computer;
    determining additional data about the mental state data wherein the additional data provides information about mental states and wherein the additional data includes information about a context as the mental state data was collected;
    tagging the additional data to the mental state data;
    interpolating the intermittent mental state data, wherein the interpolating is based on the additional data that was tagged; and
    sending at least a portion of the mental state data tagged with the additional data to a web service.

8. The method of claim 7 further comprising analyzing the mental state data to produce mental state information.

9. The method of claim 8, further comprising using the additional data in conjunction with the mental state data to produce the mental state information.

10. The method of claim 7 further comprising obtaining mental state data from a second source.

11. The method of claim 10 wherein the mental state data from the second source includes facial information.

12. The method of claim 11 wherein the mental state data from the second source includes biosensor information.

13. The method of claim 7 wherein the additional data includes information on a source that collected the mental state data.

14. The method of claim 7 wherein the context comprises a time.

15. The method of claim 7 wherein the context comprises a location.

16. The method of claim 15 wherein the location is determined using GPS.

17. The method of claim 7 wherein the context comprises environmental information.

18. The method of claim 7 wherein the context comprises an identity of another person in proximity of the individual.

19. The method of claim 7 wherein the context comprises an activity performed by the individual.

20. The method of claim 7 wherein the additional data includes information about an identity of the individual.

21. The method of claim 20 wherein the information about the identity of the individual is determined using face recognition.

22. The method of claim 7 wherein the portion of the mental state data is determined based on face recognition.

23. The method of claim 7 wherein the additional data includes human coded information on the individual.

24. A computer program product embodied in a non-transitory computer readable medium for mental state analysis, the computer program product comprising code which causes one or more processors to perform operations of:
    capturing mental state data on an individual from a first source that includes facial information, wherein the mental state data collected is intermittent;
    capturing mental state data on the individual from at least a second source that includes facial data, wherein the at least a second source comprises a mobile device, including a cell phone, a tablet computer, a wearable device, or a laptop computer;
    determining additional data about the mental state data wherein the additional data provides information about mental states and wherein the additional data includes information about a context as the mental state data was collected;
    tagging the additional data to the mental state data;
    interpolating the intermittent mental state data, wherein the interpolating is based on the additional data that was tagged; and
    sending at least a portion of the mental state data tagged with the additional data to a web service.

25. The method of claim 1 further comprising imputing additional mental state data where the mental state data is missing.

26. The method of claim 1 further comprising associating interpolated data with the mental state data that is collected on an intermittent basis.

27. The method of claim 1 where the mental state data is intermittent due to an image collection being lost.

28. The method of claim 1 wherein the sources of facial data include a wearable camera which includes glasses worn by an observer.

29. The method of claim 1 wherein mental state data is collected from multiple devices while a user is performing a task using an electronic display during a portion of time.

30. The method of claim 29 wherein the multiple devices include a tablet computer and a cell phone.

31. The method of claim 1 wherein contextual data is collected simultaneously with the mental state data.

32. The method of claim 31 wherein the contextual data includes location data, environmental information, or time data.

33. The method of claim 7 further comprising locating pertinent mental state data based on the tagging.

34. The method of claim 33 wherein the pertinent mental state data is identified for retrieval from a database.

35. The method of claim 33 further comprising sending tagged mental state data over the internet to cloud or web-based storage or web-based services for remote use and using the tags locally on a machine where the mental state data was collected.

* * * * *